(12) United States Patent
Radatti et al.

(10) Patent No.: US 7,370,795 B2
(45) Date of Patent: May 13, 2008

(54) MEDICINE MANAGEMENT METHODS AND APPARATUS

(75) Inventors: Marie D. Radatti, Conshohocken, PA (US); Peter V. Radatti, Conshohocken, PA (US)

(73) Assignee: Cybersoft, Inc., Conshohocken, PA (US)

( * ) Notice: Subject to any disclaimer, the term of this patent is extended or adjusted under 35 U.S.C. 154(b) by 50 days.

(21) Appl. No.: 11/104,330

(22) Filed: Apr. 12, 2005

(65) Prior Publication Data

US 2006/0265134 A1    Nov. 23, 2006

(51) Int. Cl.
*G06F 7/08* (2006.01)
*G06F 17/00* (2006.01)
*G06F 19/00* (2006.01)
*G06Q 10/00* (2006.01)

(52) U.S. Cl. ............... 235/381; 235/375; 235/385; 705/28

(58) Field of Classification Search .......... 235/375, 235/385, 462.01, 381; 705/28
See application file for complete search history.

(56) References Cited

U.S. PATENT DOCUMENTS

| | | | |
|---|---|---|---|
| 6,799,725 B1* | 10/2004 | Hess et al. | 235/462.01 |
| 6,848,593 B2* | 2/2005 | Papp | 221/25 |
| 6,994,249 B2* | 2/2006 | Peterka et al. | 235/375 |
| 7,059,526 B1* | 6/2006 | Sullivan et al. | 235/462.01 |
| 2001/0028308 A1* | 10/2001 | De La Huerga | 340/573.1 |

\* cited by examiner

*Primary Examiner*—Seung Ho Lee
*Assistant Examiner*—April A. Taylor
(74) *Attorney, Agent, or Firm*—John F. A. Earley, III; Frank J. Bonini, Jr.; Harding, Earley, Follmer & Frailey, P.C.

(57) ABSTRACT

Methods and apparatus are shown for providing information on a pill. A patient specific delivery apparatus for medicine using information on a pill or pills is shown as well, and a database with patient specific information may be provided, resulting in an individualized pharmacopoeia for a patient.

17 Claims, 2 Drawing Sheets

MEDICINE MANAGEMENT METHODS AND APPARATUS

The present disclosure relates to medicine management. More particularly, the present disclosure relates to medicine management methods and apparatus.

BACKGROUND

Managing medicines may be crucial to the patient. For example, properly managing the taking of medicine, because of mistakes, forgetfulness, etc., may be problematic. As another example, medicine often must be taken according to a prearranged or predetermined schedule. Managing that schedule may be difficult, however, e.g., when a patient forgets to take his or her medicine, forgets when medicine was last taken, etc. Moreover, difficulties may be compounded when multiple medicines need to be taken, thus compounding management difficulties.

Other problems may arise in addition to management problems. For example, when multiple medicines are required, interactions between the medicines must be carefully considered, as medicines may interact with each other in less than desirable fashion, which may lead to serious, unintended consequences for the patient.

DETAILED DESCRIPTION

Figure 1:
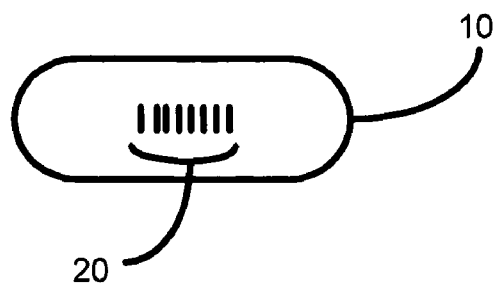
FIG. 1 shows a preferred embodiment.

FIG. 1 shows a preferred embodiment. A pill 10 is shown. Information 15 is present upon the pill.

The word "pill" is used herein to indicate a delivery system for a medicine.

The word "medicine" is used herein to include materials for diagnosing, treating, and/or preventing disease and/or other damage to a patient (including drugs, any other suitable substances, etc.,) and/or materials for supporting and/or maintaining health of a patient (including but not limited to supplements (including dietary supplements,) nutrients, vitamins, minerals, any other suitable substances, etc.)

"Delivery" is used herein to indicate the process of taking medicine.

"Delivery system" is used herein to indicate any type of delivery systems suitable for delivering medicine. For example, Oral Drug Delivery Systems, such as; Oral Controlled-Release Drug Delivery Systems, Tablets, Capsules, Coated Tablets and Capsules, Gel-Caps, Caplets, Diffusion Systems, Reservoir Systems, Chewable Tablets, Rapid Dissolving Systems, Buccal Systems, Effervescent Systems, Polymer-Based Systems, etc.; Parenteral Drug Delivery Systems, such as, Infusion Products, Supplies and Devices, IV Administration Sets, Pumps, Controllers, and Catheters, Hypodermic Products, Supplies and Devices, such as Syringes, Needles, etc., Specialized Parenteral Dosage Formulations, such as Monoclonal Antibodies, Polymers, Liposomes, Hemodialysis Products, Peritoneal Dialysis Products, Enteral Feeding Products, etc.; Inhalation Drug Delivery Systems, such as Dry Powder Inhalers, Metered Dose Inhalers, Nasal Spray Dispensers, Liquid Inhalers, Inhalation Supplies and Devices, Oxygen Therapy Equipment, Oxygen Therapy Supplies, Ventilators, Anesthesia Equipment, Anesthesia Disposables, Nebulizers, etc.; Transmucosal, Transdermal and Implantable Drug Delivery Systems, such as Transdermal Drug Delivery Systems, Transdermal Technologies, e.g., Estrogen Replacement Patches, Nicotine Patches, etc.; Implantable Drug Delivery Systems, such as Pulse Generators, Drug Inserts, Drug-Eluting Stents, etc.; Organ System Specific Drug Delivery, such as Pulmonary Drug Delivery, Nasal Delivery to Central Nervous System, Cardiovascular System, Gastro-Intestinal Tract, Genito-Urinary Tract, Ocular Drug Delivery, Controlled Release Systems, etc.; Highly Targeted Drug Delivery Systems, such as Polymer and Collagen Systems, Particle-Based Systems, Therapeutic Monoclonal Antibodies, Liposomes, Microparticles, Modified Blood Cells, Nanoparticles, Viral Assisted Intracellular Gene Delivery, Non-Viral Intracellular Gene Delivery, etc.

"Patient" is used to indicate the organism to be treated (including but not limited to human, non-human animal, any other suitable organism, etc.)

Returning now to the embodiment of FIG. 1, information 15 may be as varied as desired, as is further described below. In preferred embodiments, information 15 contains the name of the medicine (which may be scientific, generic or manufacturer specific,) the dosage embodied in the pill, lot number, serial number, and manufacturer name, printed on pill 10 in coded form. Embodiments may provide pill specific information, which is defined herein as the name of the medicine, size and/or dosage of the medicine.

The coded form used in the embodiment of FIG. 1 is bar coding. Thus, the information is readable by a bar code reader. The bar coding scheme of preferred embodiments may use predetermined coding, e.g., a numerical designation assigned to a manufacturer, a numerical designation for the name of the medicine, etc.

Information present on pills may vary as desired in various embodiments. For example, generic and/or specific information may be used. An example of generic information is information that is of interest to or about more than one specific patient, such as manufacturer name, scientific names and/or formulas, etc. An example of patient specific information is information that is of interest to or about a specific patient such as physician information, information about medical conditions, etc.

Information may be generic as well as patient specific, that is, could be present in a generic form and/or be modified to be in a patient specific form. Examples of information that may be either or both generic and patient specific are: use and/or instructional information, such as dosages, known interactions, limits, etc.; scheduling information, etc.

Information may be used as well that is already present on a pill. For example, weight, color, shape, or other suitable indicia may be used in combination with added information.

Returning to FIG. 1, in the embodiment therein, information 15 is printed on pill 10 in any suitable ink, e.g., edible soy inks, etc. In other embodiments, engraving, or any other suitable means, may be used as desired to mark a pill with desired information. For example, laser or other suitable means; masking means; ion deposit means; light wave or other electromagnetic reflection and/or refraction means which may include surface modification means; or any other suitable means. More than one marking mechanism may be used as well, as is further described below.

Marking means do not have to be exclusively external, but may also be any suitable internal means, such as doping with appropriate inert substances that suitably reflect electromagnetic waves. Internal and external means may be combined as well as desired. So, for example, an internal generic type of identification may be inserted when the medicine is formulated, and when refined into pill form, an external, patient specific type of information may be applied.

Information in various embodiments may be machine readable, or both user and machine readable. For example, bar coding techniques may be used in a machine readable embodiment, to provide appropriate information. As another example, certain information may be present in machine readable form and other information present in user readable form on the same pill.

A reader for information may be any suitable mechanism. A reader may be provided to any number of entities as desired, e.g., manufacturer, dispenser, patient, etc. Of course, one or more entities may use a reader, and some may use a reader and writer in order to both read and/or write and/or modify pill information.

It should be noted that information may also be present on a package for a pill, in addition to information on the pill. For example, rice paper wrapping or other suitable disposable and/or edible packaging may be marked.

Generally, a suitable marking mechanism is provided that will adequately convey the information to be desired. For example, generic information may be fairly simple, and so a first marking mechanism adequate to convey simple information may be used, such as a one dimensional bar code. Such information can then be used to dispense the pills in generic fashion, such as when they are sent to a pharmacy. Patient specific information may be more complicated, and so a second marking mechanism may be used, such as a two dimensional bar code or a pill wrapping.

A pharmacy, for example, may desire to add to the manufacturer's marking (in the example immediately above) patient specific marking, such as scheduling information. In this scenario, the manufacturer's markings will be machine readable, by a dispensary at the pharmacy, so that the pills are appropriately dispensed as well. The marking by the pharmacy may be either or both machine or user readable, so that the patient may be able to either i;se a local dispenser which reads the machine readable information, or read the information. (Of course, in this and other embodiments, it may be desired to modify the patient's information once it is placed on the pill if necessary, and so suitable marking should be used in those embodiments.)

It should be noted that information may be applied that is an indicator or other short form. For example, information may be applied to a pill that is an index to a database entry on an external pill reader or other suitably accessible device. Thus, the information need only be appropriately linked to that index in order to be read and disseminated to the client, such as through a printed sheet, packaging, etc. An embodiment uses an index, for example, by accessing a database in any suitable manner, and so provides the ability to read and, if desired, disseminate the information present in the database. As is further described below, in preferred embodiments, that database provides an individualized pharmacopoeia for a patient.

In preferred embodiments, therefore, information that has been present on a pill container, whether patient specific or generic, or both is transferred to the pill. The information may be transferred directly, such as when all the information is contained on the pill, or at least partially, such as when a pointer is transferred onto a pill for subsequent linkage to a database or the like. In various embodiments, information may be further customized so as to be suitable for the nature of the pill, e.g. a smaller pill may have only a pointer for a database link, a larger pill may have sufficient information to make an index unnecessary, etc.

It should be noted that various embodiments may also provide for updating. So, for example, if newly discovered information regarding pill safety or interactions or other information is made available, a database or other suitable means on the reader may be updated, and the user notified. Notification may be by any suitable means, such as when the user applies for a refill, when a scan of a pill is done, by a connection from a reader or other device and/or database to another patient communications channel (e.g., telephone, pager, email, physician, pharmacist, etc.)

In various embodiments, information may also be used to package pills in any suitable manner and/or means for a patient. For example, embodiments may provide multiple pill packages for a patient, that is, a packaging system providing all the medications for a patient to be taken at various intervals.

In certain preferred embodiments, an individualized pharmacopoeia may be provided. For example, information may be individualized for a particular patient at a manufacturer or pill dispensary, and the pills dispensed to the patient. So, for example, a pharmacist may be able to access a patient medication database, providing information on all pills for a patient, and assemble pills appropriate to a patient and/or a patient's schedule. A printed or other schedule may also be provided.

Embodiments may be especially useful for the disabled or other impaired individuals, who may not be able to take the medicine on schedule without help. Thus, various embodiments may provide for individualized delivery of a pill.

Packaging may occur using any suitable automated and/or manual means. For example, embodiments may provide a series of packages with appropriate dosages for various times for the user, e.g., one for pills to be taken at breakfast, one for pills to be taken at lunch and one for pills to be taken at supper.

Figure 2:
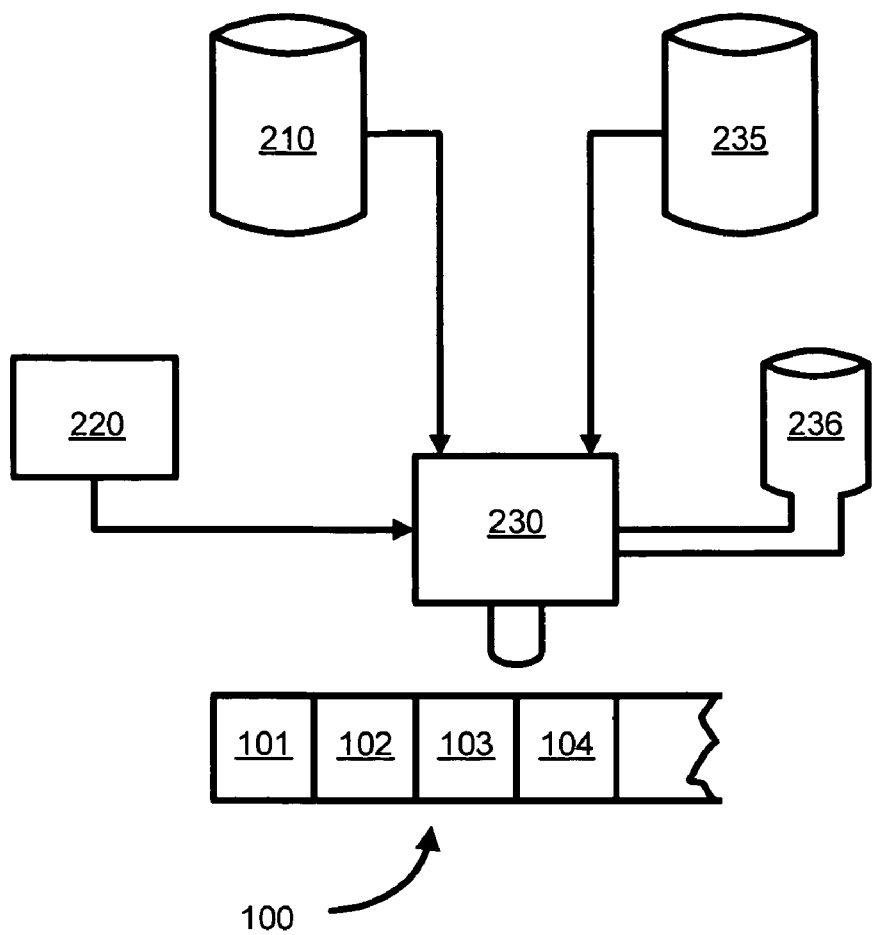
FIG. 2 shows a preferred embodiment.

Turning to FIG. 2, an embodiment is seen for individualized multiple pill management. Patient A receives a dispenser shown generally at 100. Subpackage 101 comprises pills to be taken at breakfast; Subpackage 102 comprises pills to be taken at lunch; Subpackage 103 comprises pills to be taken at dinner; Subpackage 104 comprises pills to be taken at bedtime, etc.

Package 100 is assembled by Pill Provider 220, which may be automated, manual or a combination of both. Pill Provider 220 accesses database 210 as desired. Database 210 provides information on suitable medicine, and its scheduling, for patient A. Information for the database may come from one source, e.g., HMO's, hospitals, primary health care providers, or other suitable sources, or more than one source, e.g., HMO's, hospitals, primary health care providers, or other suitable sources, and is stored in database 210 as is known in the art.

Pill Provider 220 accesses dispensary 230 as desired as well. Dispensary 230 contains one or more types of pills, such as shown in container 236, labeled as is desired with information as is desired, and is linked to a database 235 that provides pill information, so that dispensary 230 may read a pill and consult its database in order to understand the information on the pill.

Dispensary 230 reads patient A's information from database 210 and also reads or has read pill information from database 235. The appropriate pills for patient A are accessed via reading information on pills accessed by dispensary 230 and are dispensed from dispensary 130, into Subpackages 101, 102, 103, 104, etc. Each subpackage is sealed as is known in the art, after assembly.

Figure 3:
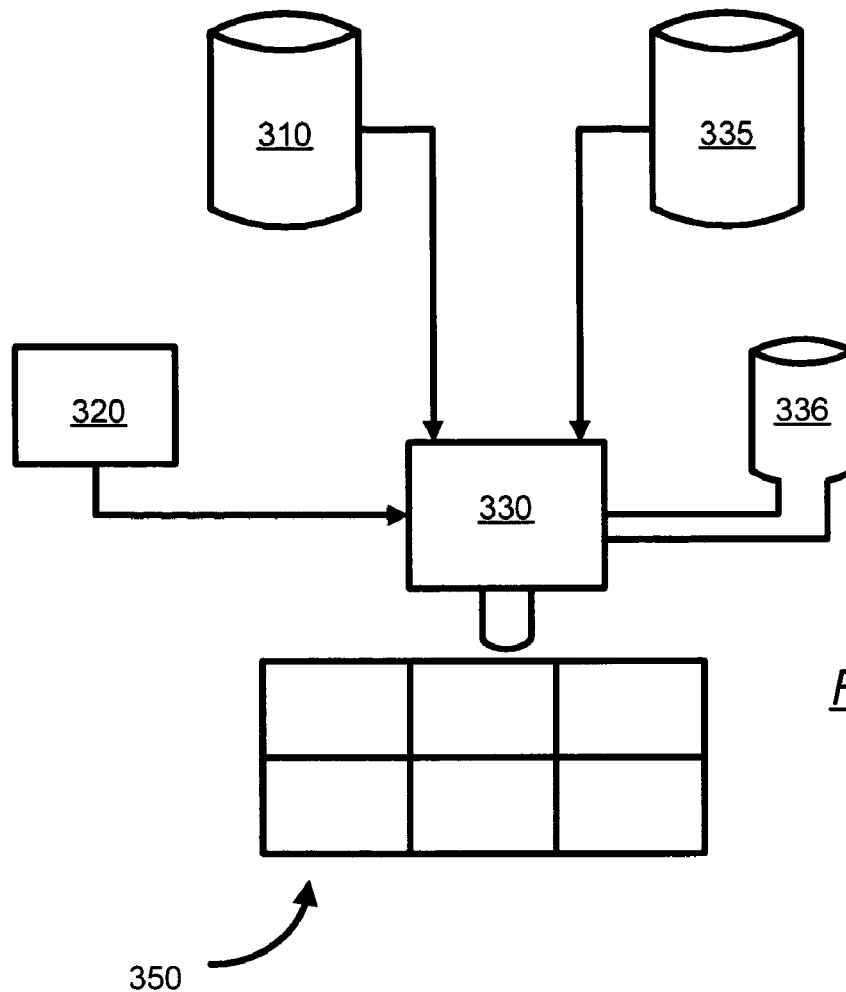
FIG. 3 shows a preferred embodiment.

FIG. 3 shows an example of another embodiment for individualized multiple pill management. Database 310 provides information on suitable medicine for patient B. Information for the database may come from one source, e.g., HMO's, hospitals, primary health care providers, or other suitable sources, or more than one source, e.g., HMO's, hospitals, primary health care providers, or other suitable sources, and is stored in database 310 as is known in the art.

Pill Provider 320, which may be automated, manual or a combination of both, accesses database 310 as desired. Pill Provider 320 accesses dispensary 330 as desired as well. Dispensary 330 contains one or more types of pills, such as shown in container 336, labeled as is desired with information as is desired, and is linked to a database 335 that provides pill information, so that dispensary 330 may read a pill and consult its database in order to understand the information on the pill.

Dispensary 330 reads patient B's information from database 310 and also reads or has read pill information from database 335. The appropriate pills for patient B are accessed via reading information on pills accessed by dispensary 330 and are dispensed from dispensary 330, into dispenser 350.

Figure 4:
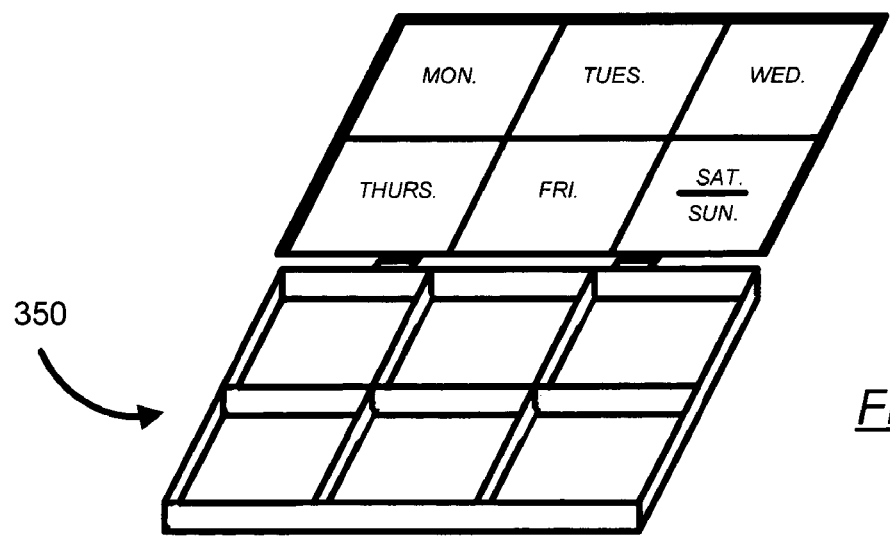
FIG. 4 shows a preferred embodiment.

Turing to FIG. 4 for a moment, an embodiment of dispenser 350 is shown. Dispenser 350 is divided into days of the week. Thus, returning to FIG. 3, dispensary 330 dispenses the appropriate medications for patient B into the appropriate day of the week divisions of dispenser 350.

Dispenser 350 is then provided to patient B, who now has a dispenser for his or her medicine with appropriate day of the week indications. Thus, in this and other embodiments, a patient's medicine may be conveniently scheduled. Of course, scheduling may be according to any desired schedule, in any desired time increments, such as days of the week, dates, times of days, weeks, months, etc.

Embodiment that provide individualized patient management may use a database of patient medications. Such a database includes patient specific information, as had been described above. It may be populated and accessed using any suitable means. So, for example, a pharmacist may access such a database and accordingly assemble a patient specific medicine or medicines, delivered in any suitable means.

A separate notification device and/or system may also be provided. For example, a patient may be notified by any suitable means to take his or her medication. Such notification may be triggered through a database link, such as a link to database 310 in FIG. 3, which also provide reminders as desired, e.g., to a patient telephone, cell phone, pager, etc.

Certain embodiments may provide alerts and/or alarms in a dispenser as well, in order to set and/or provide alerts and/or alarms to a user. For example a dispenser may provide an alert to a user at intervals to take a pill, in order to alert a user of a scheduled time for the taking of said pill. As another example a user may configure an alarm in order to provide future alerts for the taking of a pill.

One preferred embodiment provides customized dispensing for pills for hospital or other health care facilities' use. Health care facilities may have to track medicine for a number of patients and the use of a patient specific customization system and/or apparatus may be helpful So, for example, a hospital may be supplied with pills with generic information, which it can then machine read and dispense to the appropriate patients.

Customized packaging may be used as well. Embodiments may use packaging for example that is suitable for visually or otherwise impaired patients, so as to make it more convenient for a patient to determine what pills to take and when. Embodiments may assist in actually permitting pills to be picked up and ingested, for example, when a patient may have difficulty with smaller pills, etc.

Customized pill formation may be used as well. Embodiments may allow for medicine resizing and/or reformulation according to patient abilities. For example, a patient may be unable to take medicine according to a standard pill size of the medicine, such as a pill size that is too large for the patient, too small, etc. It may be possible therefore to assemble a pill, once the medicine information is provided, into a pill size that is more accessible to the patient. Thus a dispenser may substitute one size for another with appropriate information.

Yet other embodiments provide a security system for tracking medicine. Pills may be tracked according to their information. For example, an embodiment with personal information, if lost by the patient and found by another, may be tracked to the user by reading the information present on the pill. As another example, a law enforcement or other agency may track pills back to an original patient, thus possibly limiting misuse, e.g., resale, of controlled substances.

Information provided by any dispensers and/or readers may be useful as well. For example, billing records may be generated, insurance records may be kept, refills scheduled, notices provided to a patient, automated management of medicines provided, etc.

Embodiments may also reduce errors in pill dispensing. For example, pharmacies may be able to ensure that scheduled medicines are not counter indicated, physicians maybe able to ascertain that medicine combinations are effective, etc.

Any such information included herein may be, if desired, provided so as to be sufficiently protected according to appropriate regulations, e.g., privacy regulations and the like, using any suitable means.

The above description and the views and material depicted by the figures are for purposes of illustration only and are not intended to be, and should not be construed as, limitations on the invention.

Moreover, certain modifications or alternatives may suggest themselves to those skilled in the art upon reading of this specification, all of which are intended to be within the spirit and scope of the present invention as defined in the attached claims.

We claim:

1. A method for managing medicine, comprising: reading information on a pill via a reader; and, delivering a pill, the method further including:
   providing a database containing information including suitable medicine and its scheduling for a patient,
   providing a dispensary containing one or more types of pills wherein said one or more types of pills are labeled with information, and wherein said dispensary is linked to a database containing information corresponding to the information on the pill;
   reading with said dispensary said information on said pill, and
   correlating said information on said pill with said database containing information including suitable medicine and its scheduling for a patient;
   accessing appropriate pills for the patient based on correspondence of said pill information by reading information on pills; and dispensing from said dispensary said pills into one or more subpackages of a dispenser, wherein each subpackage is associated with a scheduling event, and sealing said subpackages.

2. A method as in claim 1 wherein said information is selected from the group consisting essentially of: the name of the medicine, the dosage embodied in the pill, lot number, serial number, manufacturer name, physician information, or medical condition information.

3. A method as in claim 1 comprising providing said information.

4. A method as in claim 3, where said providing is done using a technique selected from a group consisting essentially of: printing; engraving; masking; ion deposit means; surface modification means; or internal doping means.

5. A method as in claim 1, wherein said information is coded.

6. A method as in claim 5, wherein said information is bar coded.

7. A method as in claim 1 further comprising dispensing said pill from a dispenser with an alarm.

8. A method as in claim 7 further comprising configuring said alarm to provide an alert to a user in order to alert said user of a scheduled time for the taking of said pill.

9. A method for medicine management comprising: providing information on a pill; and, providing a reader for said information, where said providing is done using a technique selected from a group consisting essentially of: engraving; masking; ion deposit means; surface modification means; internal doping means; or covering said pill with an edible covering; wherein said internal doping means consists of doping with appropriate inert substances that reflect electromagnetic waves, and wherein when said providing information consists of internal doping means said reader is configured to read electromagnetic waves;

where said providing is done using at least two techniques, wherein one of said at least two techniques consists of internal doping means consisting of doping with appropriate inert substances that reflect electromagnetic waves, and wherein said at least one other of said at least two techniques is selected from the group consisting essentially of: printing; engraving; masking; ion deposit means; surface modification means; internal doping means; or covering said pill with an edible covering; and wherein said at least one technique provides information selected from at least one of the group consisting essentially of: the name of the medicine, the dosage embodied in the pill, lot number, serial number, manufacturer name, physician information, or medical condition information, and wherein the said at least one other of said at least two techniques provides information selected from at least another one of the group consisting essentially of: the name of the medicine, the dosage embodied in the pill, lot number, serial number, manufacturer name, physician information, or medical condition information.

10. A method as in claim 9, further comprising dispensing said pill from a dispenser with an alarm.

11. A method as in claim 10 further comprising configuring said alarm to provide an alert to a user in order to alert said user of a scheduled time for the taking of said pill.

12. The method of claim 9, wherein covering said pill consists of covering said pill with rice paper and wherein information is provided on said rice paper, said rice paper and information thereon being ingestible.

13. A method for medicine management comprising: providing information on a pill; and, providing a reader for said information, where said providing is done using a technique selected from a group consisting essentially of: engraving; masking; ion deposit means; surface modification means; internal doping means; or covering said pill with an edible covering; wherein said internal doping means consists of doping with appropriate inert substances that reflect electromagnetic waves, and wherein when said providing information consists of internal doping means said reader is configured to read electromagnetic waves, wherein covering said pill consists of covering said pill with rice paper and wherein information is provided on said rice paper, said rice paper and information thereon being ingestible.

14. A method as in claim 13, wherein said information is selected from the group consisting essentially of: the name of the medicine, the dosage embodied in the pill, lot number, serial number, manufacturer name, physician information, or medical condition information.

15. A method as in claim 13, comprising modifying said information.

16. A method as in claim 13, wherein said information is coded.

17. A method as in claim 16, wherein said information is bar coded.

* * * * *